United States Patent [19]
Harte et al.

[11] Patent Number: 5,017,475
[45] Date of Patent: May 21, 1991

[54] FLUORESCENT DETECTION METHOD BASED ON ENZYME ACTIVATED CONVERSION OF A FLUOROPHORE PRECURSOR SUBSTRATE

[75] Inventors: Richard A. Harte, Redwood City, Calif.; Stephen H. Mastin, Rockville, Md.

[73] Assignee: Microbiological Associates, Inc., Rockville County, Md.

[21] Appl. No.: 89,605

[22] Filed: Aug. 25, 1987

Related U.S. Application Data

[63] Continuation-in-part of Ser. No. 801,671, Nov. 25, 1985, abandoned.

[51] Int. Cl.$^5$ .................. C12Q 1/28; C12Q 1/30; G01N 33/53
[52] U.S. Cl. ............................ 435/7.9; 435/25; 435/28; 435/27; 435/7.1
[58] Field of Search ................. 435/7, 25, 27, 28, 7.9

[56] References Cited

U.S. PATENT DOCUMENTS 4,372,745  2/1983  Mandle et al. .................. 436/805

FOREIGN PATENT DOCUMENTS 1216216  1/1987  Canada .

OTHER PUBLICATIONS

Konagaya et al.—Chem. Abst. vol. 100 (1984), p. 47914z.
Lentfer—Chem. Abst. vol. 102 (1985), p. 20790k.
Hofmann et al.—Chem. Abst. vol. 99 (1983), p. 18988g.
Caillaud et al.—Chem. Abst. vol. 99 (1983), p. 84100n.

Primary Examiner—Sam Rosen
Attorney, Agent, or Firm—John P. White

[57] ABSTRACT

Methods are provided for the fluorescent detection of an analyte of interest wherein an amine-substituted, ortho-fused pyrazine fluorophore, with neither nitrogen of the pyrazine ring being fused or substituted, is produced by enzymatic oxidation of a fluorophore precursor substrate which comprises a nitrogen-substituted, cyclic compound. Also provided are novel fluorophore-labelled compounds.

29 Claims, 1 Drawing Sheet

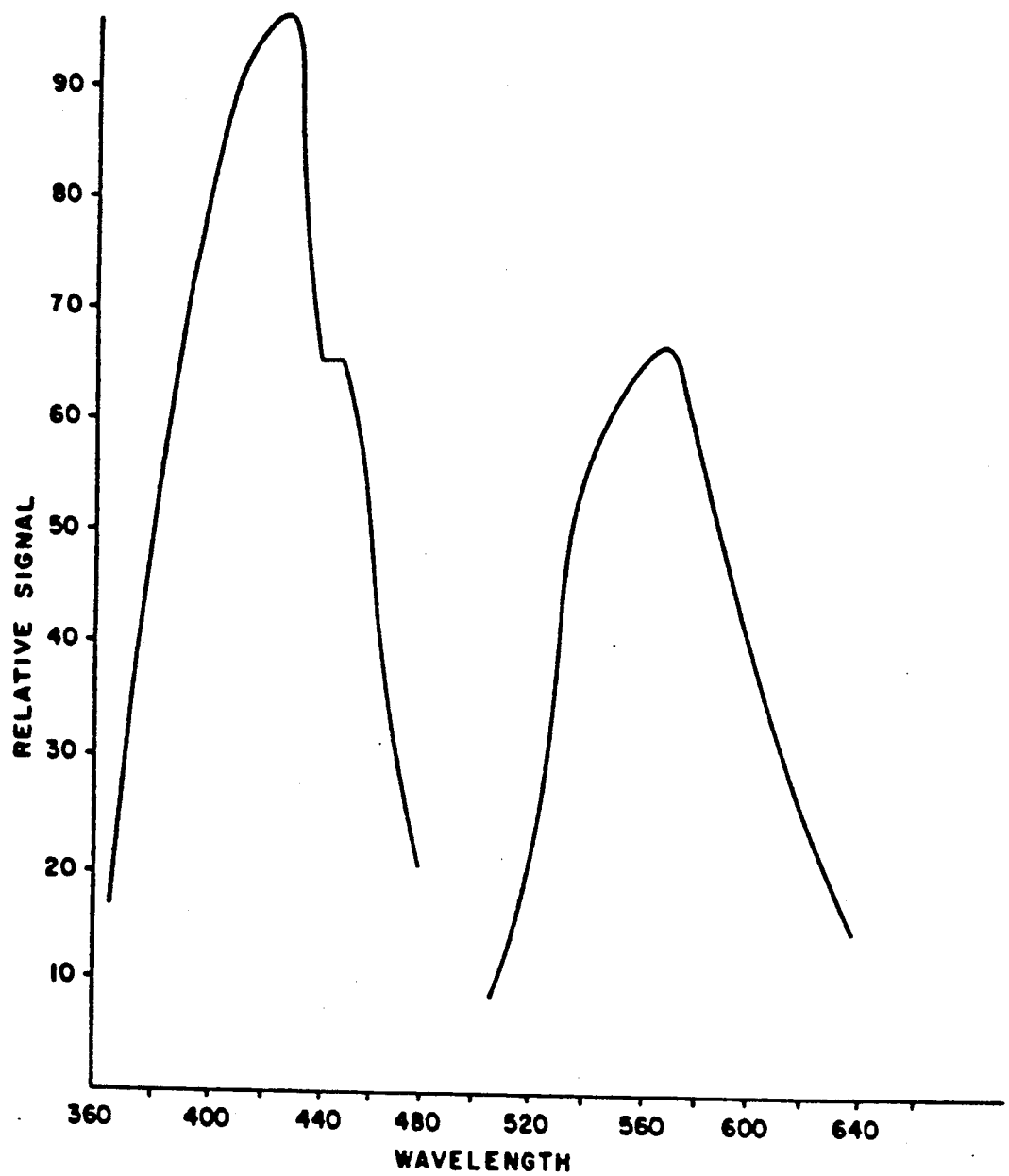

FLUORESCENT DETECTION METHOD BASED ON ENZYME ACTIVATED CONVERSION OF A FLUOROPHORE PRECURSOR SUBSTRATE

This application is a continuation-in-part of now abandoned U.S. Ser. No. 801,671, filed Nov. 25, 1985, the contents of which are hereby incorporated by reference into the subject application.

BACKGROUND OF THE INVENTION

The present invention concerns fluorescent substrates and fluorophores produced therefrom useful in fluorescent detection methods. Measurement of the fluorescence produced by these fluorophores is indicative of the presence and the amount of fluorophore in a sample.

Immunoassays employing the unique specificity of antibodies for their counterpart antigens at the molecular binding level have been demonstrated to be extremely valuable methods of analysis to determine the presence or absence of one or more components. The specificity of an antibody for its coupling partner, i.e., counterpart antigen, permits the detection of very small concentrations of specific antigens or antibodies in the presence of considerable other biomaterials (proteins, lipids, sugars, etc.) as usually found in body fluids or other biological samples.

In the past several decades, one of the more useful approaches employed to take advantage of this specificity utilizes the labeling or tagging of either the antibody or the antigen, depending upon the analyte sought in the sample. It is the label or tag which is detected in making a determination with respect to the analyte sought. Exemplary of labels that may be employed are radioactive labels which can be detected in scintillating or gamma counters, fluorochromes which can be detected in fluorometers, luminescent labels which spontaneously emit light and can be detected by light detectors, and enzymes labels which in themselves are not detectable but which, when allowed to interreact with other "substrate" molecules, produce changes in the substrate which can be detected. The advantage of the enzyme label is the fact that a single enzyme molecule can alter many tens of thousands of substrate molecules per minute, and this translates into enhanced sensitivity.

The use of enzyme labels in an assay system has been referred to as an enzyme-labelled immuno-sorbant assay, which for brevity is sometimes referred to as an ELISA technique. Such assays are the subject of a number of U.S. patents, including the following: U.S. Pat Nos. 3,654,090; 3,791,932; 3,839,153; 3,850,752; 3,879,262; 4,016,043; RE 29,169; U.S. Pat. Nos. 4,152,411; 4,169,012; 4,228,240; 4,292,403; 4,331,761; 4,343,896; RE 31,006.

In a typical ELISA technique, a binding partner for the substance to be determined is reduced to an insolubilized form, as by adsorption of the binding partner on the wall of a plastic tube or other adsorbant, i.e., reactive surface. The substance to be determined is reacted with the insolubilized binding partner and the liquid phase of the reaction is subsequently separated. The solid phase is thereafter reacted with a determined amount of coupling partner of the substance to be determined, which coupling partner has been tagged with an enzyme. A coupled product results, and to this product there is added a liquid substrate reactable with the enzyme labels or tags of the coupling partner. The presence of resulting products are usually determined by viewing the color of the liquid phase in the final reaction mixture. Additionally, a chemical stopper is often added to the reaction mixture to inhibit further enzymatic reaction. In a chromogenic detection system, this chemical stopper often produces a change in the resulting product which causes a resultant change in color for easier visual read out. Many regard the chemical stopper, often acid or alkali, not so much as a stopper but rather as a color developer or enhancer.

To obtain greater sensitivity in an enzyme immunoassay, an end product measurable by fluorescent techniques would be preferred (see K. H. Milby in "Enzyme-Mediated Immunoassay", T. T. Ngo and H. M. Lenhoff, eds. Plenum Press, New York, pp. 325-341, 1985).

Fluorescence is a process by which a molecule that is excited by light of a given wavelength emits light at a longer wavelength. The intensity of light emission from a collection of fluorescent molecules depends on:
(1) the intensity of the excitation light source;
(2) the amount of light absorbed, which according to Beer's Law, depends directly on the concentration of the fluorescent molecules present; and
(3) the efficiency with which the fluorescent molecules convert absorbed light into emitted light (the fluorescence quantum yield of the molecule).

If a constant level of excitation light intensity is maintained, emitted light intensity is directly proportional to the number of fluorescent molecules present.

Fluorescence in general is considered to be up to 100 times more sensitive than spectrophotometric techniques or other color-change detection techniques. The use of $\beta$-D-galactosidase enzyme and its fluorogenic substrate 4-methylumbelliferyl $\beta$-D-galactoside has been cited in the literature as an example of this type of assay (Ishikawa E., Imagawa M., & Hashids S., "Ultrasensitive Enzyme Immunoassay Using Fluorogenic, Lumenogenic, Radioactive and Related Substrates and Factors to Limit Sensitivity", J. Biochem 73, 1319-1321, 1973).

By using fluorescent molecules as labels in immunoassays, either directly attached to an antibody or antigen (called fluorescence immunoassay, or FIA) or as a fluorogenic substrate to detect an enzyme attached to antibody or antigen (called enzyme-linked fluorescence immunoassay, EFIA, or F-ELISA, fluorescence enzyme-linked immunosorbent assay), reagent systems and instruments have been developed which allow quantitative detection of analyte levels with high efficiency and sensitivity.

FIA has the advantages of simplicity of procedure, immediate end point measurement, and excellent reproducibility (precision) of results. EFIA offers greater sensitivity than FIA, since the catalytic activity of each enzyme label can produce up to 10,000 or more fluorophores by proper choice of fluorophore precursor molecule, i.e., fluorogenic substrate. Among the fluorescent molecules most frequently used in immunochemistry are fluorescein, the rhodamines, certain coumarin (umbelliferone) derivatives, and most recently, the phycobiliproteins.

Fluorescein is currently the label of choice in FIA. Its physical properties illustrate the factors important in a fluorophore label. Fluorescein is a very efficient emitter of light, with a fluorescence quantum yield of 0.3 to 0.95 (vs. the maximum possible of 1.0) when conjugated (attached) to an antibody or antigen. It is also an efficient absorber of light, with a molar extinction coefficient [related to the probability of absorbing a photon that strikes the fluorescein] of 70,000.

Fluorescein is stable and undergoes little degradation (photobleaching or photolability) when exposed to light. Techniques for labelling antibodies or protein antigens with fluorescein are relatively simple, but are not easy to control. Fluorescein's fluorescence efficiency is affected very little by temperature, but only the dianion form of the molecule, which exists above pH 8, emits strongly, i.e., fluorescence efficiency varies considerably with pH except at pH 8 or above.

On the negative side, fluorescein emits at 525 nm, with most efficient excitation at 490 nm. Its fluorescence signal is thus subject to the following types of interference which limit its effective sensitivity: (1) overlap by endogeneous fluorescence, i.e. light emitted by sustenances such as bilirubin and hemoglobin, which are normally found in serum samples; (2) quenching, e.g., by bilirubin; and (3) inner filter effects, i.e. preferential absorption of incident light by other molecules such as hemoglobin. Its small Stoke's shift (30 nm) also leads to significant background scattering, which must be eliminated by using complex, dedicated (and thus expensive) filter systems and/or by sacrificing certain efficiencies in instrument design, e.g., off-peak excitation or emission detection. Fluorescein also self-quenches (inhibits its own fluorescence) if molecules are brought into close proximity, so multiple labeling even of large molecules like antibodies is of limited use, even though fluorescein is a small molecule.

Other fluorophores also have certain advantages and drawbacks. The rhodamines fluoresce at long wavelengths, but have poor Stoke's shifts, relatively low fluorescence quantum yields, and are extremely sensitive to pH and other environmental effects. The coumarins have relatively large Stoke's shifts and high extinction coefficients but low quantum yields, are pH sensitive, and their emission is above 500 nm, i.e., subject to endogenous sample interference.

The biliproteins have very high extinction coefficients, long wavelength emission, and in the case of R-phycoerythrin, good Stoke's shifts. They also display high quantum yields, and their emission is relatively insensitive to environment within the pH range of 5.5 to 9. These molecules are large proteins which must be isolated, e.g., from red algae. One such biliprotein, R-phycoerythrin, can provide sensitivity 10–20 times greater than that afforded by fluorescein in FIA systems. Nevertheless the large size and high molecular weight of these molecules, particularly of R-phycoerythrin, place significant limitations on applications of these molecules in immunoassays because of effects on reaction kinetics; e.g., they can't be used to replace fluorescein in fluorescence polarization or in hapten assays with competitive binding formats.

SUMMARY OF THE INVENTION

The present invention provides a method for detecting an analyte of interest in a liquid sample. This method comprises contacting the sample with a first reagent capable of forming a complex with the analyte of interest so as to form a first reagent:analyte complex. The first reagent:analyte complex is then contacted with an oxidase-labelled reagent cable of forming a complex with the first reagent:analyte complex so as to form a first reagent:analyte:oxidase-labelled reagent complex. The first reagent:analyte: oxidase-labelled reagent complex is next treated with a nitrogen-substituted, cyclic compound and an oxidizing agent so as to enzymatically oxidize the nitrogen-substituted, cyclic compound to produce an amine-substituted, ortho-fused pyrazine wherein neither nitrogen of the pyrazine ring is fused or substituted. By exciting the amine-substituted, ortho-fused pyrazine so as to cause it to fluoresce, and thus to emit radiation, and detecting the radiation so emitted, the analyte of interest is detected.

The present invention also provides a method for detecting an analyte of interest present in a liquid sample. This method comprises contacting the sample with an oxidase-labelled reagent capable of competing with the analyte of interest for binding sites on a complementary material not normally present in the sample, and with the complementary material, the contact being effected under appropriate conditions such that the analyte of interest and the oxidase-labelled reagent competitively bind to the complementary material so as to form analyte of interest: complementary material complexes and oxidase-labelled reagent:complementary material complexes. The analyte of interest: complementary material complexes and the oxidase-labelled reagent: complementary material complexes are separated from unbound analyte of interest and unbound oxidase-labelled regent so as to obtain a mixture of analyte of interest: complementary material complexes and oxidase-labelled reagent: complementary material complexes. This mixture is then treated with a nitrogen-substituted, cyclic compound and an oxidizing agent so as to enzymatically oxidize the nitrogen-substituted, cyclic compound to produce an amine-substituted, ortho-fused pyrazine wherein neither nitrogen of the pyrazine ring is fused or substituted. By exciting the amine-substituted, ortho-fused pyrazine so as to cause it to fluoresce and thus to emit radiation, and detecting the radiation so emitted, the analyte of interest is detected.

A method for detecting a single-stranded nucleic acid sequence of interest in a liquid sample is also provided by the present invention. The method comprises contacting the liquid sample with an oxidase-labelled, single-stranded nucleic acid sequence complementary to the nucleic acid sequence of interest under hybridizing conditions so as to form an oxidase-labelled, double-stranded nucleic acid sequence. The oxidase-labelled, double-stranded nucleic acid sequence is treated with a nitrogen-substituted, cyclic compound and an oxidizing agent so as to enzymatically oxidize the nitrogen-substituted, cyclic compound to produce an amine-substituted, ortho-fused pyrazine wherein neither nitrogen of the pyrazine ring is fused or substituted. The amine-substituted, ortho-fused pyrazine is then excited so as to cause it to fluoresce and thus to emit radiation, the radiation so emitted is detected, and the analyte of interest is thereby detected.

The present invention also provides a method for detecting oxidase activity in a liquid sample which comprises treating the liquid sample with a nitrogen-substituted, cyclic compound and an oxidizing agent under conditions such than an oxidase present in the liquid sample enzymatically oxidizes the nitrogen-substituted, cyclic compound to produce an amine-substituted, ortho-fused pyrazine wherein neither nitrogen of the pyrazine ring is fused or substituted. The amine-substituted, ortho-fused pyrazine is then excited so as to cause it to fluoresce and thus to emit radiation; and the radiation so emitted is detected, thereby detecting oxidase activity in the liquid sample.

Also provided by the present invention is a method for detecting an oxidizing agent in a liquid sample. This method comprises treating the liquid sample with a nitrogen-substituted, cyclic compound and an oxidase under conditions such that the nitrogen-substituted, cyclic compound is enzymatically oxidized to produce an amine-substituted, ortho-fused pyrazine wherein neither nitrogen of the pyrazine ring is fused or substituted. The amine-substituted, ortho-fused pyrazine is then excited so as to cause it to fluoresce and thus to emit radiation, and the radiation so emitted is detected, thereby detecting the oxidizing agent.

The present invention also provides compounds having the structure

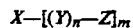

wherein:

X represents one or more nucleotides which may be the same or different, one or more amino acids which may be the same or different, an antigen, an antibody, an analyte of interest or analog of an analyte of interest;

Y represents a linker arm attaching X to Z;

Z represents an amine-substituted, ortho-fused pyrazine wherein neither pyrazine nitrogen is fused or substituted;

n represents an integer; and m represents an integer greater than or equal to 1.

Such compounds are useful as fluorophore-labelled reagents in immunoassays, nucleic acid hybridization assays, etc.

BRIEF DESCRIPTION OF THE FIGURE

FIG. 1 graphically sets forth the results obtained from the experiment described in Example 3. The plot which appears on the right of FIG. 1 illustrates the strength of fluorescent emission of different wavelengths using an excitation wavelength of 425 nm. The plot on the left of FIG. 1 is the excitation spectrum observed for an emission wavelength of 570 nm.

DETAILED DESCRIPTION OF THE INVENTION

The present invention provides a method for detecting an analyte of interest in a liquid sample. This method comprises contacting the sample with a first reagent capable of forming a complex with the analyte of interest so as to form a first reagent:analyte complex. The first reagent:analyte complex is then contacted with an oxidase-labelled reagent capable of forming a complex with the first reagent:analyte complex so as to form a first reagent: analyte: oxidase-labelled reagent complex. The first reagent:analyte: oxidase-labelled reagent complex is next treated with a nitrogen-substituted, cyclic compound and an oxidizing agent so as to enzymatically oxidize the nitrogen-substituted, cyclic compound to produce an amine-substituted, ortho-fused pyrazine wherein neither nitrogen of the pyrazine ring is fused or substituted. Within the present application, "cyclic compound" means an alicyclic or heterocyclic compound. By exciting the amine-substituted, ortho-fused pyrazine so as to cause it to fluoresce, and thus to emit radiation, and detecting the radiation so emitted, the analyte of interest is detected.

In one embodiment of the invention, the first reagent: analyte: oxidase-labelled reagent complex is treated with at least two structurally different nitrogen-substituted, cyclic compounds. In another embodiment of the invention, the first reagent:analyte:oxidase-labelled reagent complex is treated with the nitrogen-substituted, cyclic compound and the oxidizing agent under conditions wherein the pH is within the range from about 3.5 up to about 6.5, preferably within the range from about 4.5 to about 5.0

In still another embodiment of the invention the analyte of interest is an antigen and the first reagent and the oxidase-labelled reagent are antibodies, ligands, or haptens. In yet a further embodiment of the invention, the analyte of interest is an antibody and the first reagent and the oxidase-labelled reagent are antigens, haptens, ligands, antibodies, or anti-idiotypic antibodies.

The present invention also provides a method for detecting an analyte of interest present in a liquid sample. This method comprises contacting the sample with an oxidase-labelled reagent capable of competing with the analyte of interest for binding sites on a complementary material not normally present in the sample, and with the complementary material, the contact being effected under appropriate conditions such that the analyte of interest and the oxidase-labelled reagent competitively bind to the complementary material so as to form analyte of interest: complementary material complexes and oxidase-labelled reagent:complementary material complexes. The analyte of interest: complementary material complexes and the oxidase-labelled reagent: complementary material complexes are separated from unbound analyte of interest and unbound oxidase-labelled reagent so as to obtain a mixture of analyte of interest: complementary material complexes and oxidase-labelled reagent: complementary material complexes. This mixture is then treated with a nitrogen-substituted, cyclic compound and an oxidizing agent so as to enzymatically oxidize the nitrogen-substituted, cyclic compound to produce an amine-substituted, ortho-fused pyrzaine wherein neither nitrogen of the pyrazine ring is fused or substituted. By exciting the amine-substituted, ortho-fused pyrazine so as to cause it to fluoresce and thus to emit radiation, and detecting the radiation so emitted, the analyte of interest is detected.

In one embodiment of the invention, the analyte of interest is an antigen, the oxidase-labelled reagent is the antigen or an analog of the antigen conjugated to an oxidase, and the complementary material is an antibody, ligand, or hapten. In another embodiment of the invention the analyte of interest is an antibody, the oxidase-labelled reagent is the same or a different antibody conjugated to an oxidase, and the complementary material is an antigen, hapten, ligand, antibody, or anti-idiotypic antibody. In yet another embodiment of the invention, the mixture is treated with at least two structurally different nitrogen-substituted, cyclic compounds.

A method for detecting a single-stranded nucleic acid sequence of interest in a liquid sample is also provided by the present invention. The method comprises contacting the liquid sample with an oxidase-labelled, single-stranded nucleic acid sequence complementary to the nucleic acid sequence of interest under hybridizing conditions so as to form an oxidase-labelled, double-stranded nucleic acid sequence. The oxidase-labelled, double-stranded nucleic acid sequence is treated with a nitrogen-substituted, cyclic compound and an oxidizing agent so as to enzymatically oxidize the nitrogen-substituted, cyclic compound to produce an amine-substituted ortho-fused pyrzaine wherein neither nitrogen of the pyrazine ring is fused or substituted. The amine-substituted, ortho-fused pyrazine is then excited so as to cause it to fluoresce and thus to emit radiation, and the radiation so emitted is detected, thereby detecting the analyte of interest.

In one embodiment of the invention, the oxidase-labelled, single-stranded nucleic acid sequence is treated with at least two structurally different nitrogen-substituted, cyclic compounds.

The present invention also provides a method for detecting oxidase activity in a liquid sample which comprises treating the liquid sample with a nitrogen-substituted, cyclic compound and an oxidizing agent under conditions such that an oxidase present in the liquid sample enzymatically oxidizes the nitrogen-substituted, cyclic compound to produce an amine-substituted, ortho-fused pyrazine wherein neither nitrogen of the pyrazine ring is fused or substituted. The amine-substituted, ortho-fused pyrazine is then excited so as to cause it to fluoresce and thus to emit radiation; and the radiation so emitted is detected, thereby detecting oxidase activity in the liquid sample.

In one embodiment of the invention, the liquid sample is treated with at least two structurally different nitrogen-substituted, cyclic compounds.

Also provided by the present invention is a method for detecting an oxidizing agent in a liquid sample. This method comprises treating the liquid sample with a nitrogen-substituted, cyclic compound and an oxidase under conditions such that the nitrogen-substituted, cyclic compound is enzymatically oxidized to produce an amine-substituted, ortho-fused pyrzaine wherein neither nitrogen of the pyrazine ring is fused or substituted. The amine-substituted, ortho-fused pyrzaine is then excited so as to cause it to fluoresce and thus to emit radiation, and the radiation so emitted is detected, thereby detecting the oxidizing agent.

In one embodiment of the invention, the liquid sample is treated with at least two structurally different nitrogen-substituted, cyclic compounds.

The methods provided by the present invention may be practiced by oxidizing the nitrogen-substituted, cyclic compound so as to form an amine-substituted, ortho-fused pyrazine which comprises an aminophenazine. Additionally, the methods provided by the present invention may be practiced by enzymatically oxidizing a nitrogen-substituted cyclic compound which comprises an amine-substituted or imine-substituted cyclic compound. Moreover, the nitrogen-substituted cyclic, compound which is oxidized may comprise an amine-substituted aromatic compound. In one embodiment of the invention the amine-substituted, aromatic compound is an ortho-substituted, diamino-aromatic compound. In another embodiment of the invention the ortho-substituted, diamino-aromatic compound is 1,2-diaminobenzene (also known as o-phenylenediamine and referred to herein as OPD), 3,4-diaminobenzoic acid, or 2,3-diaminopyridine.

The methods provided by the present invention may be performed qualitatively or quantitatively. Moreover, prior to exciting the amine-substituted, ortho-fused pyrazine so as to cause it to fluoresce, the pH may be adjusted to greater than about 6.5. In one embodiment of the invention, the pH is adjusted to greater than about 10 prior to exciting the amine-substituted, ortho-fused pyrazine so as to cause it to fluoresce.

The oxidase utilized in the methods provided by the present invention may be a peroxidase or catalase. In one embodiment of the invention, the peroxidase may be horseradish peroxidase. Additionally, the oxidizing agent may be a peroxide, e.g. hydrogen peroxide or urea peroxide.

The present invention also provides a compound having the structure

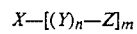

$$X-[(Y)_n-Z]_m$$

wherein:

X represents one or more nucleotides which may be the same or different, one or more amino acids which may be the same or different, an antigen, an antibody, an analyte of interest or analog of an analyte of interest;

Y represents a linker arm attaching X to Z;

Z represents an amine-substituted, ortho-fused pyrazine wherein neither pyrazine nitrogen is fused or substituted;

n represents an integer; and m represents an integer greater than or equal to 1.

This compound is useful as a fluorophore-labelled reagent in immunoassays, nucleic acid hybridization assays, etc.

In one embodiment of the invention, Z represents 2,3-diaminophenazine, 2,3-diamino-1,8-diazaphenazine, 6,7-diamino-1,5-diazaphenazine, or 2,3-diaminophenazine-6-carboxylic acid.

The methods and compounds provided by the present invention are based upon the fluorescent detection of a fluorophore which is produced by the enzymatic oxidation of a fluorophore precursor substrate. These novel methods and compounds will be better understood by reference to the following examples which are provided for purposes of illustration and are not to be construed as in any way limiting the scope of the present invention, which is defined by the claims appended hereto.

EXAMPLES

EXAMPLE 1

Serial dilutions were prepared of various substances, and samples of these serial dilutions were tested for fluorescence activity in a fluorimeter. The excitation wavelength bandpass in the fluorimeter was 450±20 mn. The emission wavelength bandpass in the fluorimeter was 550±20 nm. Readings were obtained in fluorescent signal units. The following table sets forth the reading results obtained, with the specific substance analyzed being listed under the column labelled "Substance" and with the different dilutions of the samples being indicated at the heads of the columns set forth to the right of the "Substance" column. The fluorescent signal unit reading indicated for substance #7 was in excess of 8192, 8192 being the maximum fluorescent signal unit reading available with the fluorimeter.

TABLE I

| Substance | Dilution | | |
|---|---|---|---|
| | 1:10 | 1:100 | 1:1000 |
| 1. 1,2-diaminobenzene (3.2 mM in phosphate buffered saline solution pH 7) | 727 | — | 528 |
| 2. hydrogen peroxide (0.01% aqueous solution) | 661 | 700 | 756 |
| 3. horseradish peroxidase-labelled avidin (1:1000 in phosphate buffered saline solution) | 502 | 501 | 455 |

TABLE I-continued

| Substance | Dilution | | |
|---|---|---|---|
| | 1:10 | 1:100 | 1:1000 |
| 4. 1,2-diaminobenzene with hydrogen peroxide (3.2 mM in phosphate buffered saline solution pH 7 with 0.1% $H_2O_2$) | 570 | 537 | 498 |
| 5. 50 microliters 1,2-diaminobenzene (3.2 mM in phosphate buffered saline solution pH 7) plus 50 microliters peroxidase-labelled avidin (1:1000 in phosphate buffered saline solution) | 941 | 769 | 538 |
| 6. hydrogen peroxide plus peroxidase-labelled avidin (1:1000 in phosphate buffered saline solution with 0.01% $H_2O_2$) | 568 | 732 | 538 |
| 7. 50 microliters 1,2-diaminobenzene with hydrogen peroxide (3.2 mM in phosphate buffered saline solution pH 7 with 0.01% $H_2O_2$) plus 30 microliters peroxidase-labelled avidin (1:1000 in phosphate buffered saline solution) | >8192 | >8192 | >8192 |
| 8. Mixture of #7 plus 100 microliters 3N HCl stopper | 900 | 838 | 1200 |

It will be seen from Table I that various ingredients employed in carrying out the method of the invention by themselves or in various subcombinations displayed only marginal fluorescence reactivity. On the other hand, the reaction product produced by the action of peroxidase-labelled avidin on the substrate 1,2-diaminobenzene in the presence of a hydrogen peroxide oxidizer resulted in a fluorescence reactivity exceeding the measurement capability of the fluorimeter even at serial dilution of 1:1000.

EXAMPLE 2

To determine the structure of the fluorophore produced by oxidation of OPD with HRP and hydrogen peroxide, a reaction mixture containing the fluorophore was concentrated to give a crop of dark brown needles, which were then isolated from the concentrated solution by filtration. The resulting dark brown needles were dissolved in butyl alcohol, applied to a KBr plate and allowed to dry. An IR spectrum of the sample was recorded using an IBM FTIR spectrometer.

The recorded spectral data indicated the presence of unsubstituted amino groups, as well as an aromatic heterocyclic compound which contains nitrogen. This data indicated that the reaction mixture contained 2,3-diaminophenazine (DAP).

Authentic 2,3-diaminophenazine and 2,2'-diaminoazobenzene were chemically synthesized by standard literature methods (see Gupta and Srivastava, Indian J. Chem. 9:1303-1304, 1971 and Omote, et al., Chemistry and Industry, p. 996, 1971, respectively).

Product formation from the enzymatic oxidation of OPD using 0.1 M sodium citrate, pH 5, 0.005 M hydrogen peroxide, 100 ng/ml HRP and 0.015 M OPD was monitored by thin layer chromotography on Kieselgel® 60$F_{254}$ silica gel plates (E. M. Scientific, N.J.) using the solvent system benzene:ethanol:acetone:0.25% ammonium hydroxide (100:30:5:2). Additionally, authentic DAP, 2,2'-diaminoazobenzene and the starting material OPD were run on the plates. Only one product was observed from the enzymatically oxidized reaction mixture of OPD. This product had an $R_f$ value identical to that of authentic DAP and fluoresced strongly under a black light.

The reaction mixture described above was diluted 1/50 in 0.1 M sodium citrate, pH 5, and its emission spectrum was obtained and compared with that of authentic DAP ($1.3 \times 10^{-5}$ M) in 0.1 M sodium citrate, pH 5. Using an excitation wavelength of 440 nm on a McPherson Model FL750 spectrofluorimeter, the maximum wavelength of emission for authentic DAP was 565 nm compared with 562 nm for the OPD reaction mixture.

These data indicate that the product of enzymatic oxidation of OPD is DAP and, further, that the DAP product is responsible for the observed fluorescence.

EXAMPLE 3

A reacted mixture of 1,2-diaminobenzene, hydrogen peroxide, and peroxidase-labelled avidin (substance #7 in Table I) was analyzed in an Aminco-Bowman scanning spectrofluorimeter to determine fluorescence reactivity in response to a given excitation wavelength, and to determine the excitation spectrum for a fluorescent emission of a given wavelength. As may be seen with reference to FIG. 1, peak emission was observed at the wavelength 565 nm with an optimum excitation wavelength of 415 nm. A Stoke's shift of 150 nm in the sample analyzed was demonstrated.

In Table II below, the Stoke's shifts experienced with some of the more commonly known fluorophores is set forth and compared with the Stoke's shift demonstrated with diaminophenazine.

TABLE II

| Fluorophore | Excitation (nm) | Emission (nm) | Stoke's Shift (nm) |
|---|---|---|---|
| Fluorescein | 495 | 525 | 30 |
| Tetramethyl-rhodamine | 550 | 585 | 35 |
| 4-methyl umbelliferone | 375 | 450 | 75 |
| Fluorescamine | 394 | 475 | 81 |
| Lucifer yellow VS | 430 | 540 | 110 |
| R-phycoerythrin | 495 | 575 | 80 |
| Diaminophenazine | 415 | 565 | 150 |

EXAMPLE 4

Serial dilutions (in phosphate buffered saline solution) of anti-feline IgG antibody labelled with horseradish peroxidase were reacted with 1,2-diaminobenzene and hydrogen peroxide (3.2 mM with 0.01% $H_2O_2$) in a series of glass test tubes. After a five minutes reaction, 20 microliters of each tube'2 contents were transferred to wells in a plastic tray. The contents of these wells were then read in a fluorimeter for fluorescence quantitation. Table III below sets forth the respective dilutions of the antibody and the fluorimeter reading obtained.

TABLE III

| Dilution of Anti-Feline IgG Antibody | Fluorimeter Reading | Visual Subjective Fluorescence Under Black Lamp (Wavelength of 365 nm) |
| --- | --- | --- |
| 1. 1:800 | 8192+ | 4+ |
| 2. 1:3200 | 5195 | 2+ |
| 3. 1:12800 | 4400 | 2+ |
| 4. 1:51000 | 3705 | 2+ |
| 5. 1:204000 | 2743 | 2+ |
| 6. 1:816000 | 1525 | 0 |
| 7. Buffer | 611 | 0 |

Also indicated in Table III is the visual subjective fluorescence observed under a black lamp, with grading being done on a zero to four basis, zero being no observed fluorescence and four being indicative of clearly observed and distinct fluorescence of high intensity.

EXAMPLE 5

Three-fold serial dilutions were prepared from $D.immitis$ (Heartworm) antigen (2 mg per ml) beginning with a 1:10 dilution in 0.01 M carbonate-bicarbonate buffer, pH 9. Five microliters of each antigen dilution were applied as spaced droplet deposits along the surface of a nitrocellulose strip. The strips were then incubated at 37° C. for thirty minutes and washed with phosphate buffered saline solution pH 7.0 containing 0.3% ovalbumin and 0.05% Tween (detergent).

Dilutions were prepared of dog anti-$D.immitis$ IgG (1:50, 1:250, 1:1250, and 1:6250) in the phosphate buffered saline solution described. Each antibody dilution was used in the soaking of a strip containing each antigen dilution. The strips were then incubated for one hour at room temperature.

Biotin-labelled goat anti-dog antibody IgG diluted 1:100 in the above-described phosphate buffered saline solution was then applied to the deposits on the various strips and the strips incubated for one hour at room temperature. The strips were then washed for fifteen minutes with phosphate buffered saline solution.

The assay was then developed by overlaying the deposits with horseradish peroxidase-labelled avidin diluted 1:3000 in phosphate buffered saline solution and the strips incubated for one hour. The strips were then washed with phosphate buffered saline solution.

Each of the deposits was then punched out of the nitrocellulose strips using a paper punch, and the punched deposits placed in respective wells of a carrier such as a Track XI ® microtiter strip (Microbiological Associates, Inc., Bethesda, MD) described in U.S. Pat. No. 4,468,371 and DES 279,817. Twenty microliter volumes of 1,2-diaminobenzene and hydrogen peroxide solution (3.2 mM with 0.01% $H_2O_2$) were placed in the wells and the reaction allowed to proceed for five minutes. The contents of the various wells were then washed with water.

The discs of cellulose then analyzed in a fluorimeter utilizing an excitation wavelength of 450±20 nm and an emission wavelength bandpass of 550±20 nm. The discs were also usually analyzed to determine subjectively fluorescence under a black light (360 nm), and to determine fluorescence with a fluorescence microscope with blue excitation and green filter in the eye piece. Table IV sets forth the fluorimeter readings obtained in signal units for the various deposits, and the subjective fluorescence noted.

TABLE IV

| Well | Fluorimeter Reading | Black Light Subjective Fluorescence | Microscope-Subjective Fluorescence |
| --- | --- | --- | --- |
| 1 | 5301 | 4+ | 4+ |
| 2 | 2718 | — | ± |
| 3 | 4623 | 4+ | 5+ |
| 4 | 2429 | 1+ | ± |
| 5 | 2786 | — | ± |
| 6 | 5718 | 3+ | 4+ |
| 7 | 6026 | 2+ | 3+ |
| 8 | 5862 | 3+ | 2+ |
| 9 | 2508 | — | ± |

EXAMPLE 6

Clear polypropylene capillary tubes were precoated with a 5% polycarbonate polymer (Lexan) in methylene dichloride solvent. After evaporation of the solvent, a uniformly thin polymeric transparent film of the polycarbonate was left as a residual on the inner surfaces of the tubes.

A dilution of unlabeled antibody directed against herpes simplex virus (diluted in 0.01 M carbonate-bicarbonate buffer pH 9) was then adsorbed on the coated inner surfaces of the capillary tubes with insolubilizing of the antibody.

After adsorption of the capture antibody and washing with phosphate buffered saline solution pH 7, serial dilutions of herpes virus antigen extracted from tissue culture and suspended in phosphate buffered saline solution were drawn up into the interior of the tubes and the tubes and their contents incubated for thirty minutes. The tubes were then emptied and flushed with phosphate buffered saline solution.

A dilution of a second antibody to herpes simplex virus labelled with biotin (1:1000 in phosphate buffered saline solution) was then passed through the tubes. This was followed with another wash with phosphate buffered saline solution, and the introduction to the interior of the tubes of an avidin-labelled horseradish peroxidase solution (1:1000 dilution in phosphate buffered saline solution). After a fifteen minute incubation and washing with phosphate buffered saline solution, a mixture of 1,2-diaminobenzene and hydrogen peroxide (3.2 mM with 0.01% $H_2O_2$) was drawn in to the interior of the tubes. After a ten minute reaction period, the contents of the tubes were transferred to test wells and fluorescence reactivity determined with a fluorimeter using an excitation wavelength bandpass of 450±20 nm and an emission wavelength bandpass of 550±20 nm. Subjective fluorescence utilized black light was also determined. Table V summarizes the results obtained.

TABLE V

| Dilution of HSV-I Solution | Subjective Fluorescence Black Light (360 nm) | Fluorescence Signal Units |
| --- | --- | --- |
| 1:1,000 | 4+ | 6103 |
| 1:10,000 | 4+ | 3609 |
| 1:100,000 | 3+ | 1530 |
| 1:1,000,000 | 2+ | 1910 |
| Diluent only | ± | 1250 |
| No sample | 0 | 1022 |

EXAMPLE 7

Wells of polystyrene microtiter plates were sensitized for sixteen hours at 4° C. with a 1:750 dilution of rabbit antibody directed against the specific bacterial protein F-1 of *Yersine pestis* (plague) diluted in 0.01 M carbonate-bicarbonate buffer pH 9.

After adsorption of the captured antibody and a thorough washing with phosphate buffered saline solution, 100 microliter aliquots of serial diluted *Y. pestis* antigen (diluted in phosphate buffered saline solution) were introduced to the wells and the wells and their contents incubated at room temperature for one hour. Following another phosphate buffered saline solution wash, 100 microliter aliquots of a 1:8000 dilution (in phosphate buffered saline solution) of mouse monoclonal antibody directed against the F-1 antigen of *Y. pestis* were introduced to the wells and the wells and the contents incubated for one hour at room temperature.

After a thorough wash with phosphate buffered saline solution, goat anti-mouse antibody labelled with horseradish peroxidase and diluted 1:8000 in phosphate buffered saline solution was introduced to the wells through adding 100 microliters of the dilution to each well. The wells and their contents were then incubated for thirty minutes, after which the contents of the wells were discarded and the wells washed with phosphate buffered saline solution. A mixture of 1,2-diaminobenzene and hydrogen peroxide (3.2 mM with 0.01% $H_2O_2$) in 100 microliter amounts was then added to each well and the plates incubated for ten minutes at room temperature.

The liquid contents of the various wells were then read for fluorescence emission in a fluorescence microtiter plate reader, with excitation at 450±20 nm, and emission quantitated at 550±20 nm. Table VI summarizes the results obtained.

TABLE VI

| Well | Antigen Dilution | Antigen Concentration | Fluorescence Signal Units |
|---|---|---|---|
| 1 | 1:50 | 20 micrograms/ml | 4722 |
| 2 | 1:250 | 4 micrograms/ml | 4261 |
| 3 | 1:1250 | 800 nanograms/ml | 4365 |
| 4 | 1:7250 | 160 nanograms/ml | 3973 |
| 5 | 1:36250 | 32 nanograms/ml | 2490 |
| 6 | 1:181250 | 6 nanograms/ml | 2723 |
| 7 | Diluent | 0 | 2699 |

It should be obvious from the above that a novel enzyme-labelled detection method has been described which relies upon the action of the enzyme in the labelled material to produce a fluorophore whose presence is detectable using fluorescent measuring techniques. The fluorophore disclosed exhibits a large Stoke's shift, with the wavelength of the light producing excitation of the fluorophore being substantially different than the wavelength of the emitted light produced. The method contemplated is extremely sensitive, relying as it does upon an enzyme-labelled immunoreagent and the interreaction of such immunoreagent on a substrate to produce a produce which is detectable using fluorescent techniques. An assay performed pursuant to the invention may be relatively easily performed. The fluorophore which is produced as the reaction product from the substrate may be detected either as part of the liquid phase in the final mixture produced, or as a residual which clings to the reaction surface confining the ingredients which partake in the reactions involved (solid phase).

EXAMPLE 8

The effects of base addition to a horseradish peroxidase:peroxide: OPD system were examined by adding NaOH to the system to terminate the horseradish peroxidase reaction at various time intervals. Specifically, positive and negative control wells were prepared by immobilizing polyclonal antibodies specific for feline leukemia virus p27 antigen to the wells of a COLLIMMUNE ® coated Track XI ® microtiter strip (Microbiological Associates, Inc., Bethesda, MD) described in U.S. Pat. No. 4,468,371 and DES 279,817. Twenty microliters of a cocktail containing three biotinylated monoclonal antibodies specific for the FeLV p27 antigen were added to each well. Twenty microliters of negative calibrator serum containing no FeLV p27 antigen were added to the negative control wells and 20 microliters of high calibrator serum containing FeLV p27 antigen were added to the positive control wells. Samples were incubated for 15 min. at room temperature, washed with deionized water, dried, and 20 microliters of avidin-labelled horseradish peroxidase (HRP) were added to each well. The samples were incubated for 10 min. at room temperature, washed and dried. Twenty microliters of a solution containing urea peroxide and OPD (0.5 mg/ml) in cirtate buffer (pH 5) were added to each well and allowed to incubate for 5 minutes, at which time the fluorescence of each well was read (t=0). Immediately upon completion of fluorescence measurement of each well, 20 microliters of 2 N NaOH were added to each well to adjust the pH to greater than or equal to 10. At 1 and 4 minutes respectively, the fluorescence measurement of each well was again determined.

TABLE VIII

| | FSU Negative Control (N) | FSU Positive Control (P) | ΔFSU (P-N) |
|---|---|---|---|
| t = 0 min (pH = 5) | 1202 | 4766 | 3564 |
| t = 1 min (pH ≧ 10) | 1491 | 6814 | 5323 |
| t = 4 min (pH ≧ 10) | 1375 | 6626 | 5251 |

The data in Table VIII illustrate the effect of NaOH addition to the OPD-DAP reaction.

The data in Table VIII indicate that base addition enhances the ΔFSU (FSU=arbitrary fluorescence unit), by increasing the FSU of the positive sample by approximately 50% without significantly affecting the FSU of the negative sample. The data also indicate that ΔFSU is stable over time after base addition, indicating that the enzymatic reaction has been stopped.

EXAMPLE 9

Another compound which is enzmatically oxidized by HRP and $H_2O_2$ or urea peroxide to yield a fluorophore is 3,4-diaminobenzoic acid (DABA).

DABA forms the following aminophenazine upon enzymatic oxidation with HRP and urea peroxide or hydrogen peroxide, which fluoresces at about 540 nm with an optimum excitation at about 430 nm. This fluorophore is 2,3-diaminophenazine-6-carboxylic acid.

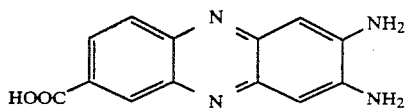

Applications have used DABA as the substrate in the immunoassay for the feline leukemia virus antigen described in Example 8, substituting DABA for OPD in the reaction buffer. One pair of reaction wells was simultaneously run using OPD (0.5 mg/ml) as the substrate. To the remaining wells were added various concentrations of DABA from 0.125 mg/ml to 2 mg/ml.

A positive standard and a negative standard were prepared for each concentration of DABA and fluorescence was measured using a TRACK XI ®MP fluorimeter. Fluorescence measurements were made for each reaction well as a function of time over approximately 20 minutes. Twenty microliters 2 N NaOH were added to each well to adjust the pH to greater than or equal to about 10, and the fluorescence of each well was read again. Finally, wells were washed, dried, and fluorescence measurements were made on the substrate (COL-LIMUNE ®). Data are summarized in Table IX below.

TABLE IX

| ΔFSU = (FSU, pos sample) - (FSU, neg sample) | | | | | |
|---|---|---|---|---|---|
| | Reaction time | | | After Quench | After Wash, On Solid |
| | 4 min | 8 min | 13 min | 18 min | NaOH | Phase |
| DABA, 0.125 mg/ml | — | 27 | 44 | 64 | — | — |
| DABA, 0.25 mg/ml | 42 | 89 | 138 | 191 | 82 | 97 |
| DABA, 0.5 mg/ml | 48 | 157 | 253 | 339 | 145 | 191 |
| DABA, 1 mg/ml | 69 | 224 | 352 | 461 | 274 | 308 |
| DABA, 2 mg/ml | 70 | 262 | 405 | 531 | 385 | 474 |
| OPD, 0.5 mg/ml | 1750 | 4020 | 5463 | 6745 | >7590 | >7023 |

The FSU reading between positive samples and negative samples increased with both time and increasing substrate concentration. These data demonstrates that a reaction occurs between the bound HRP label and the DABA substrate and that the enzyme reaction may be stopped with base.

EXAMPLE 10

Another compound which is enzmatically oxidized by HRP and hydrogen peroxide or urea peroxide to yield a fluorophore is 2,3-diaminopyridine (DAPY)

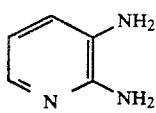

DAPY forms at least two different fluorescent products, depending on substrate and peroxidase concentration. At high concentration of HRP or DAPY, a product is produced which, at pH 5, fluoresces at 585 nm. Optimum excitation for this compound occurs at 435 nm.

At low concentration of DAPY and HRP, a product is produced which, at a pH greater than or equal to 10, emits at 530 nm, with excitation at 437 nm. Applicants contemplate that these reaction products are 2,3-diamino-1,8-diazaphenazine

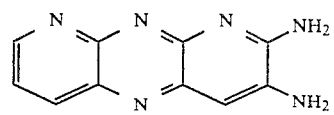

and 6,7-diamino-1,5-diazaphenazine

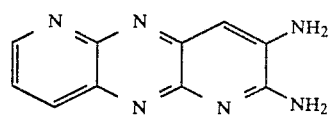

EXAMPLE 11

Applicants contemplate the use of multiple component substrate systems which include any combination of nitrogen-substituted, cyclic compound substrates which, as single components may or may not be enzmatically oxidized to form amine-substituted, ortho-fused pyrazines wherein neither nitrogen of the pyrazine ring is fused or substituted, but which form chimeric, i.e., hybrid, fluorophores when enzymatically oxidized as a mixture.

Examples of such multicomponent substrate systems contemplated include:
(1) OPD and DAPY;
(2) OPD and DABA;
(3) DAPY and DABA;
(4) 4,5-diaminopyrimidine and 3-aminopyrazine-2 carboxylic acid;
(5) 4-amino-2,1,3-benzothiadizole and 2-aminobenzimidazole; and
(6) 9,10-diaminophenanthrene and aniline.

EXAMPLE 12

The use of DAP as a fluorophore label has been demonstrated by preparing an SPDP [N-sucinimidyl 3-(2-pyridyldithio)propionate] conjugate of DAP with antimouse IgG antibody. This conjugate was prepared as follows:

DAP was dissolved in ethanol to give a saturated solution, i.e., about 0.3 mg/ml DAP. Rabbit anti-mouse IgG antibody was dissolved in phosphate buffered saline (PBS) to give a concentration of 5 mg/ml antibody. SPDP was dissolved in ethanol to a concentration of 0.040 M.

250 microliters of the SPDP solution were added to 250 microliters of the DAP solution and separately to 250 microliters of the anti-mouse IgG solution. The two solutions were reacted simultaneously for 30 min, after which each was loaded onto a G-25 Sephadex column.

The IgG reaction mixture was eluted from the column with 0.1 M PBS; the DAP reaction mixture was eluted from the column with 0.1 M acetate buffer containing 0.1 M NaCl and 0.05 M dithiothreitol (DTT). The eluants were then allowed to react for 25 minutes at room temperature, after which each was again separately loaded onto a G25 Sephadex column and eluted as above. One hundred microliters of each eluant were mixed together and allowed to react at 4° C. overnight to form a DAP-antimouse IgG conjugate. The solution containing the conjugate was used without further purification.

Twenty microliters each of mouse serum containing low and high titers of antibodies to mouse hepatitis virus (MHV) antigen were added to COLLIMMU-NE® coated wells of a Track XI® microtiter strip containing immobilized MHV antigen and allowed to react for 10 min. at room temperature. The wells were washed and dried, and 20 microliters of serially diluted DAP-anti-mouse IgG conjugate were added to each well and allowed to incubate for 10 min. at room temperature.

Wells were washed, dried and fluorescence measurements were made on each well using a Track XI®MP fluorescence reader (see Table X for results).

TABLE X

| Conjugate dilution | FSU, low | FSU, high | ΔFSU |
| --- | --- | --- | --- |
| 1/50 | >8200 | >8200 | — |
| 1/100 | >8200 | >8200 | — |
| 1/200 | >8200 | >8200 | — |
| 1/400 | 5618 | >8200 | >2380 |
| 1/800 | 3454 | >8200 | >4746 |
| 1/1600 | 2237 | 5481 | 3244 |

The differential fluorescence between wells containing low and high titers of antibodies to MHV when reacted with the highly diluted conjugate solution demonstrates that there is specific reactivity of a fluorescent conjugate molecule and that the conjugated DAP-moiety retains its fluorescent properties.

EXAMPLE 13

DAP may be reacted with uridine-2'-hemisuccinate in dimethylformamide and the reaction mixture subsequently analyzed by thin layer chromatography. When observed under a black light, one product is observed. This product is the DAP amide of uridine-2'-hemisuccinate.

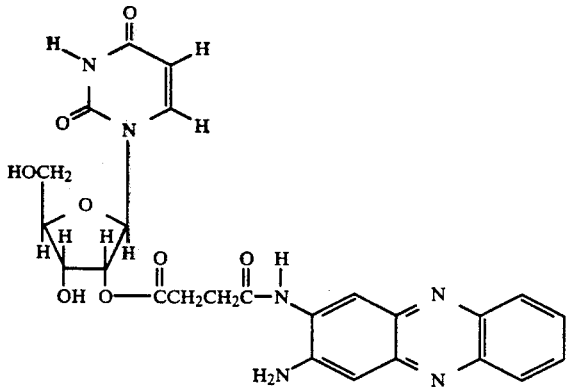

What is claimed is:

1. A method for detecting an analyte of interest in a liquid sample which comprises:
   (a) contacting the sample with a first reagent capable of forming a complex with the analyte of interest so as to form a first reagent:analyte complex;
   (b) contacting the first reagent:analyte complex with an oxidase-labelled reagent capable of forming a complex with the first reagent:analyte complex so as to form a first reagent:analyte:oxidase-labelled reagent complex;
   (c) treating the first reagent:analyte: oxidase-labelled reagent complex with a nitrogen-substituted, cyclic compound and an oxidizing agent so as to enzymatically oxidize the nitrogen-substituted, cyclic compound to produce an amine-substituted, ortho-fused pyrazine wherein neither nitrogen of the pyrazine ring is fused or substituted; and
   (d) exciting the amine-substituted, ortho-fused pyrazine so as to cause it to fluoresce and thus to emit radiation;
   (e) detecting the radiation so emitted, thereby by detecting the analyte of interest.

2. A method according to claim 1, wherein the first reagent: analyte: oxidase-labelled reagent complex is treated with at least two structurally different nitrogen-substituted, cyclic compounds.

3. A method according to claim 1, wherein the first reagent:analyte:oxidase-labelled reagent complex is treated under conditions wherein the pH is within the range from about 3.5 up to about 6.5.

4. A method according to claim 3, wherein the first reagent: analyte:oxidase-labelled reagent complex is treated under conditions wherein the pH is within the range from about 4.5 up to about 5.0.

5. A method according to claim 1, wherein the analyte of interest is an antigen and the first reagent and the oxidase-labelled reagent are antibodies, ligands or haptens.

6. A method according to claim 1, wherein the analyte of interest is an antibody and the first reagent and the oxidase-labelled reagent are antigens, haptens, ligands, antibodies, or anti-isotopic antibodies.

7. A method for detecting an analyte of interest present in a liquid sample which comprises:
   (a) contacting the sample with an oxidase-labelled reagent capable of competing with the analyte of interest for binding sites on a complementary material not normally present in the sample, and with the complementary material, the contact being effected under appropriate conditions such that the analyte of interest and the oxidase-labelled reagent competitively bind to the complementary material so as to form analyte of interest: complementary material complexes and oxidase-labelled reagent: complementary material complexes;
   (b) separating the analyte of interest: complementary material complexes and the oxidase-labelled reagent: complementary material complexes from unbound analyte of interest and unbound oxidase-labelled reagent so as to obtain mixture of analyte of interest: complementary material complexes and oxidase-labelled reagent: complementary material complexes;
   (c) treating the mixture with a nitrogen-substituted, cyclic compound and an oxidizing agent so as to enzymatically oxidize the nitrogen-substituted, cyclic compound to produce an amine-substituted, ortho-fused pyrazine wherein neither nitrogen of the pyrazine ring is fused or substituted;
(d) exciting the amine-substituted, ortho-fused pyrazine so as to cause it to fluoresce and thus to emit radiation; and
(e) detecting the radiation so emitted, thereby by detecting the analyte of interest.

8. A method according to claim 7, wherein the analyte of interest is an antigen, the oxidase-labelled reagent is the antigen or an analog of the antigen conjugated to an oxidase, and the complementary material is an antibody, ligand, or hapten.

9. A method according to claim 7, wherein the analyte of interest is an antibody, the oxidase-labelled reagent is the same or a different antibody conjugated to an oxidase, and the complementary material is an antibody, hapten, ligand, antibody, or anti-idiotypic antibody.

10. A method according to claim 7, wherein the mixture is treated with at least two structurally different nitrogen-substituted, cyclic compounds.

11. A method for detecting a single-stranded nucleic acid sequence of interest in a liquid sample which comprises:
(a) contacting the liquid sample with an oxidase-labelled, single-stranded nucleic acid sequence complementary to the nucleic acid sequence of interest under hybridizing conditions so as to form an oxidase-labelled, double-stranded nucleic acid sequence;
(b) treating the oxidase-labelled, double-stranded nucleic acid sequence with a nitrogen-substituted, cyclic compound and an oxidizing agent so as to enzymatically oxidize the nitrogen-substituted, cyclic compound to produce an amine-substituted, ortho-fused pyrazine wherein neither nitrogen of the pyrzaine ring is fused or substituted;
(d) exciting the amine-substituted, ortho-fused pyrazine so as to cause it to fluoresce and thus to emit radiation; and
(e) detecting the radiation so emitted, thereby by detecting the analyte of interest.

12. A method according to claim 11, wherein the oxidase-labelled, double-stranded nucleic acid sequence is treated with at least two structurally different nitrogen-substituted, cyclic compounds.

13. A method for detecting oxidase activity in a liquid sample which comprises:
(a) treating the liquid sample with a nitrogen-substituted, cyclic compound and an oxidizing agent under conditions such that an oxidase present in the liquid sample enzymatically oxidizes the nitrogen-substituted, cyclic compound to produce an amine-substituted, ortho-fused pyrazine wherein neither nitrogen of the pyrzaine ring is fused or substituted;
(d) exciting the amine-substituted, ortho-fused pyrazine so as to cause it to fluoresce and thus to emit radiation; and
(e) detecting the radiation so emitted, thereby by detecting oxidase activity in the liquid sample.

14. A method for detecting an oxidizing agent in a liquid sample which comprises:
(a) treating the liquid sample with a nitrogen-substituted, cyclic compound and an oxidase under conditions such that the nitrogen-substituted, cyclic compound is enzymatically oxidized to produce an amine-substituted, ortho-fused pyrazine wherein neither nitrogen of the pyrzaine ring is fused or substituted;
(d) exciting the amine-substituted, ortho-fused pyrazine so as to cause it to fluoresce and thus to emit radiation; and
(e) detecting the radiation so emitted, thereby by detecting the oxidizing agent.

15. A method according to claims 13 or 14, wherein the liquid sample is treated with at least two structurally different nitrogen-substituted, cyclic compounds.

16. A method according to claims 1, 7, 11, 13 or 14, wherein the amine-substituted, ortho-fused pyrzaine is an aminophenazine.

17. A method according to claims 1, 7, 11, 13 or 14, wherein the nitrogen-substituted cyclic compound is an amine-substituted or imine-substituted cyclic compound.

18. A method according to claims 1, 7, 11, 13 or 14, wherein the nitrogen-substituted cyclic compound is an amine-substituted aromatic compound.

19. A method according to claim 18, wherein the amine-substituted aromatic compound is an ortho-substituted, diamino-aromatic compound.

20. A method according to claim 19, wherein the ortho-substituted, diamino-aromatic compound is 1,2-diaminobenzene, 3,4-diaminobenzoic acid, or 2,3-diaminopyridine.

21. A method according to claims 1, 7, 11, 13 or 14, wherein the detection is performed qualitatively.

22. A method according to claims 1, 7, 11, 13 or 14, wherein the detection is performed quantitatively.

23. A method according to claims 1, 7, 11, 13 or 14, wherein prior to exciting the amine-substituted, ortho-fused pyrazine so as to cause it to fluoresce, the pH is adjusted to greater than about 6.5.

24. A method according to claims 1, 7, 11, 13 or 14, wherein prior to exciting the amine-substituted, ortho-fused pyrzaine so as to cause it to fluoresce, the pH is adjusted to greater than about 10.

25. A method according to claims 1, 7, 11, 13 or 14, wherein the oxidase is a peroxidase or catalase.

26. A method according to claim 25, wherein the peroxidase is horseradish peroxidase.

27. A method according to claims 1, 7, 11, 13 or 14, wherein the oxidizing agent is a peroxide.

28. A method according to claim 27, wherein the peroxide is hydrogen peroxide.

29. A method according to claim 27, wherein the peroxide is urea peroxide.

* * * * *